(12) United States Patent
Kitamura

(10) Patent No.: US 11,098,267 B2
(45) Date of Patent: Aug. 24, 2021

(54) PERFUME COMPOSITION

(71) Applicant: Mitsubishi Gas Chemical Company, Inc., Chiyoda-ku (JP)

(72) Inventor: Mitsuharu Kitamura, Niigata (JP)

(73) Assignee: Mitsubishi Gas Chemical Company, Inc., Chiyoda-ku (JP)

(*) Notice: Subject to any disclaimer, the term of this patent is extended or adjusted under 35 U.S.C. 154(b) by 0 days.

(21) Appl. No.: 16/881,513

(22) Filed: May 22, 2020

(65) Prior Publication Data
US 2020/0283696 A1    Sep. 10, 2020

Related U.S. Application Data

(63) Continuation of application No. 16/332,316, filed as application No. PCT/JP2017/030796 on Aug. 28, 2017, now abandoned.

(30) Foreign Application Priority Data

Sep. 15, 2016 (JP) .............................. JP2016-180434
Sep. 15, 2016 (JP) .............................. JP2016-180435
Sep. 15, 2016 (JP) .............................. JP2016-180436

(51) Int. Cl.
| | |
|---|---|
| *C11B 9/00* | (2006.01) |
| *A61K 8/37* | (2006.01) |
| *A23L 2/56* | (2006.01) |
| *A23L 27/20* | (2016.01) |
| *A61Q 13/00* | (2006.01) |
| *C11D 3/50* | (2006.01) |
| *C07C 69/753* | (2006.01) |
| *C07C 69/757* | (2006.01) |
| *A61K 47/14* | (2017.01) |

(52) U.S. Cl.
CPC .............. *C11B 9/0046* (2013.01); *A23L 2/56* (2013.01); *A23L 27/20* (2016.08); *A23L 27/203* (2016.08); *A61K 8/37* (2013.01); *A61K 47/14* (2013.01); *A61Q 13/00* (2013.01); *C07C 69/753* (2013.01); *C07C 69/757* (2013.01); *C11B 9/00* (2013.01); *C11D 3/50* (2013.01); *A23V 2002/00* (2013.01); *C07C 2602/42* (2017.05)

(58) Field of Classification Search
CPC .................................................. C11B 9/0046
See application file for complete search history.

(56) References Cited

U.S. PATENT DOCUMENTS

| | | | |
|---|---|---|---|
| 4,218,347 A | 8/1980 | Naf et al. | |
| 4,319,036 A | 3/1982 | Klemarczyk et al. | |
| 4,357,253 A * | 11/1982 | Klemarczyk | C07C 45/62 |
| | | | 510/105 |
| 4,374,054 A | 2/1983 | Klemarczyk et al. | |
| 4,649,214 A * | 3/1987 | Gladfelter | C07C 69/757 |
| | | | 528/74 |
| 4,661,285 A | 4/1987 | Harris et al. | |
| 5,126,065 A | 6/1992 | Tsubouchi et al. | |
| 2010/0093580 A1 * | 4/2010 | Closson | C11B 9/0046 |
| | | | 510/105 |

FOREIGN PATENT DOCUMENTS

| | | |
|---|---|---|
| JP | 54-52065 A | 4/1979 |
| JP | 57-8757 A | 1/1982 |
| JP | 60-190738 A | 9/1985 |
| JP | 62-149643 A | 7/1987 |
| JP | 62-277963 A | 12/1987 |

OTHER PUBLICATIONS

International Search Report dated Sep. 26, 2017 in PCT/JP2017/030796 filed Aug. 28, 2017.
Nakajima, M., ed., "Koryo to Choko no Kisochiski (Basic Knowledge of Perfume and Aroma Blending)," 1995, pp. 215, 235, 244-247, Sangyo Tosho K.K. (8 total pages).
Jerry, P, et al. "Synthesis of odoriferous compounds by Diels-Alder reaction", Database CA [Online] Chemical Abstracts Service, XP-002792347, 1987, 2 pages.
McCluskey, A. et al. "Inhibition of Protein Phosphatase 2A by Cantharidin Analogues", Bioorganic & Medicinal Chemistry Letters, Pergamon, vol. 6, No. 9, 1996, pp. 1025-1028.
Krapcho, A. P. et al. "Stereochemistry of Decarbalkoxylation of Cyclic Geminal Diesters Effected by Water and Lithium Chloride in $Me_2SO^1$", Journal of Organic Chemistry, XP-55598987, Vo. 45, No. 21, 1980, pp. 4105-4111.
Database Registry [Online] Chemical Abstracts Service, XP-002792348, Feb. 22, 2008, 1 page.

* cited by examiner

*Primary Examiner* — Arrie L Reuther
(74) *Attorney, Agent, or Firm* — Oblon, McClelland, Maier & Neustadt, L.L.P.

(57) ABSTRACT

A perfume composition containing a compound represented by the following formula (1):

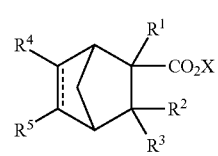

(1)

AA wherein $R^1$, $R^2$ and $R^3$ are independently hydrogen or a methyl group, X is an alkyl group having 1 to 4 carbon atoms, $R^4$ and $R^5$ are independently hydrogen or a —CHO group, and AA is a single bond or a double bond, has an excellent aroma and aroma persistence useful as a compound perfume material.

20 Claims, No Drawings

PERFUME COMPOSITION

CROSS REFERENCE TO RELATED APPLICATIONS

This application is a continuation application of prior U.S. application Ser. No. 16/332,316, filed Mar. 11, 2019, the disclosure of which is incorporated herein by reference in its entirety. U.S. Ser. No. 16/332,316 is the National stage of PCT/JP2017/030796 filed Aug. 28, 2017, the disclosure of which is incorporated herein by reference in its entirety. U.S. Ser. No. 16/332,316 claims priority to Japanese Application No. 2016-180434, Japanese Application No. 2016-180435 and Japanese Application No. 2016-180436, which were all filed Sep. 15, 2016, the disclosures of which are incorporated herein by reference in their entireties.

TECHNICAL FIELD

The present invention relates to a perfume composition.

BACKGROUND ART

It is known that some esters are compounds useful as perfumes. For example, Non Patent Literature 1 states that geranyl acetate having a rose-like aroma, methyl jasmonate having a jasmine-like sweet aroma, fruitate having a fruity aroma, methyl benzoate having an intense dry fruity aroma and the like are useful as compound perfume materials.

CITATION LIST

Non Patent Literature

Non Patent Literature 1: "Koryo to Choko no Kisochishiki (Basic Knowledge of Perfume and Aroma Blending)", edited by Motoki Nakajima, 1995, pp. 215, 235, 244-246, Sangyo Tosho K.K.

SUMMARY OF INVENTION

Technical Problem

An object of the present invention is to provide a perfume composition useful as a compound perfume material and having an excellent aroma and aroma persistence.

Solution to Problem

The present inventor took an interest in a fact that many compounds having a polycyclic structure among terpenes have excellent aromas, and synthesized various compounds having a polycyclic structure to evaluate their aromas, resulting in finding that norbornane-2-carboxylic acid ester compounds have excellent aromas and are excellent as compound perfumes, and thus, the present invention was accomplished.

Specifically, the present invention provides the following:

[1]

A perfume composition comprising a compound represented by the following formula (1):

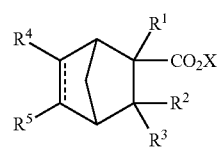

(1)

wherein $R^1$, $R^2$ and $R^3$ are independently hydrogen or a methyl group,

X is an alkyl group having 1 to 4 carbon atoms, and $R^4$ and $R^5$ are independently hydrogen or a —CHO group, and

- - - - is a single bond or a double bond.

[2]

The perfume composition according to [1], wherein the compound represented by formula (1) is one or more selected from the group consisting of the following formulas (1-1) to (1-3):

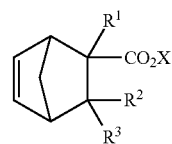

(1-1)

wherein $R^1$, $R^2$ and $R^3$ are independently hydrogen or a methyl group, and X is an alkyl group having 1 to 4 carbon atoms,

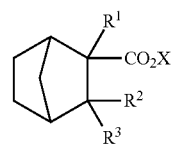

(1-2)

wherein $R^1$, $R^2$ and $R^3$ are independently hydrogen or a methyl group, and X is an alkyl group having 1 to 4 carbon atoms,

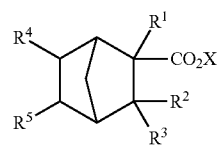

(1-3)

wherein $R^1$, $R^2$ and $R^3$ are independently hydrogen or a methyl group,

X is an alkyl group having 1 to 4 carbon atoms, and either one of $R^4$ and $R^5$ is hydrogen and the other is a —CHO group.

[3]

A perfumery and cosmetics product, a health and hygiene material, a miscellaneous good, a drink, a food, a quasi-drug or a pharmaceutical, comprising the perfume composition according to [1] or [2].

Advantageous Effects of Invention

A perfume composition of the present invention comprising a norbornane-2-carbyxlic acid ester compound has an excellent aroma and excellent aroma persistence, and hence is useful as a perfuming ingredient for a variety of products including toiletries, soap and laundry detergents.

DESCRIPTION OF EMBODIMENTS

Now, an embodiment for practicing the present invention (hereinafter simply referred to as the "present embodiment") will be described in detail. The present embodiment described below is intended to be illustrative and not restrictive for limiting the present invention to the following description. The present invention can be appropriately modified within the scope thereof.

[Perfume Composition]

A perfume composition of the present embodiment comprises a norbornane-2-carboxylic acid ester compound, namely, a compound represented by formula (1).

The perfume composition of the present embodiment may be a perfume composition comprising, as a principal component, single one or two or more compounds represented by formula (1), or may be a perfume composition comprising single one or two or more of compounds represented by formula (1) in combination with another perfume component or a compound perfume having a desired composition usually used.

The term "comprising, as a principal component, single one or two or more compounds represented by formula (1)" refers to that compounds represented by formula (1) are comprised in an amount of usually 85% by mass or more, preferably 90% by mass or more, more preferably 96% by mass or more, and further preferably 98% by mass or more with respect to a total amount of the perfume composition.

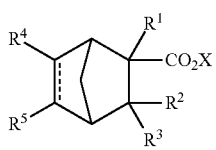

(1)

In formula (1), $R^1$, $R^2$ and $R^3$ are independently hydrogen or a methyl group, X is an alkyl group having 1 to 4 carbon atoms, and $R^4$ and $R^5$ are independently hydrogen or a —CHO group, and

‒ ‒ ‒ ‒ is a single bond or a double bond.

The compounds represented by formula (1) of the present embodiment are preferably compounds represented by the following formulas (1-1) to (1-3). The compounds represented by formulas (1-1) to (1-3) may be used singly or in combinations of two or more.

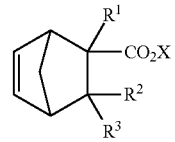

(1-1)

In formula (1-1), $R^1$, $R^2$, $R^3$ and X have the same meaning as $R^1$, $R^2$, $R^3$ and X in formula (1).

Specifically, $R^1$, $R^2$ and $R^3$ are independently hydrogen or a methyl group, and X is an alkyl group having 1 to 4 carbon atoms.

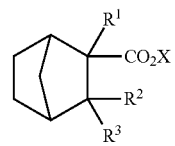

(1-2)

In formula (1-2), $R^1$, $R^2$, $R^3$ and X have the same meaning as $R^1$, $R^2$, $R^3$ and X in formula (1).

Specifically, $R^1$, $R^2$ and $R^3$ are independently hydrogen or a methyl group, and X is an alkyl group having 1 to 4 carbon atoms.

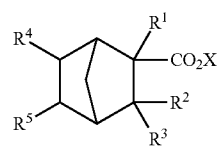

(1-3)

In formula (1-3), $R^1$, $R^2$, $R^3$ and X have the same meaning as $R^1$, $R^2$, $R^3$ and X in formula (1).

Specifically, in formula (1-3), $R^1$, $R^2$ and $R^3$ are independently hydrogen or a methyl group, and X is an alkyl group having 1 to 4 carbon atoms.

Either one of $R^4$ and $R^5$ is hydrogen, and the other is a —CHO group.

In formula (1) and formulas (1-1) to (1-3), $R^1$, $R^2$ and $R^3$ are independently hydrogen or a methyl group.

$R^2$ and $R^3$ are preferably hydrogen.

In formula (1) and formulas (1-1) to (1-3), X is an alkyl group having 1 to 4 carbon atoms. Examples of the alkyl group having 1 to 4 carbon atoms include a methyl group, an ethyl group, an n-propyl group, an iso-propyl group, an n-butyl group, an iso-butyl group and a tert-butyl group. X is preferably a methyl group or an ethyl group.

The compound represented by any of formula (1) and formulas (1-1) to (1-3) may be any single substance out of optical isomers based on asymmetric carbon whose configuration is not shown, or may be a mixture of any of these in an arbitrary ratio.

The compound represented by formula (1-1) is preferably any one of norbornene-2-carboxylic acid methyl ester, norbornene-2-carboxylic acid ethyl ester, norbornene-2-methyl-2-carboxylic acid methyl ester and norbornene-2-methyl-2-carboxylic acid ethyl ester, and more preferably any one of norbornene-2-carboxylic acid methyl ester and norbornene-2-methyl-2-carboxylic acid methyl ester.

The compound represented by formula (1-1) of the present embodiment has an aroma including both an intense ripe banana and melon-like fruity note and an ozone-like marine note, or an aroma including both a fresh floral green note and a fruity note, and is also excellent in persistence.

The compound represented by formula (1-2) is preferably any one of norbornane-2-carboxylic acid methyl ester, norbornane-2-carboxylic acid ethyl ester, norbornane-2-methyl-2-carboxylic acid methyl ester and norbornane-2-methyl-2-carboxylic acid ethyl ester, and more preferably any one of norbornane-2-carboxylic acid methyl ester and norbornane-2-methyl-2-carboxylic acid methyl ester.

The compound represented by formula (1-2) of the present embodiment has a herbal green-like aroma with a fruity note, and is also excellent in persistence.

The compound represented by formula (1-3) is preferably any one of formylnorbornane-2-carboxylic acid methyl ester, formylnorbornane-2-carboxylic acid ethyl ester, formylnorbornane-2-methyl-2-carboxylic acid methyl ester and formylnorbornane-2-methyl-2-carboxylic acid ethyl ester, and more preferably any one of formylnorbornane-2-carboxylic acid methyl ester and formylnorbornane-2-methyl-2-carboxylic acid methyl ester.

The compound represented by formula (1-3) of the present embodiment has a novel aroma including all of an intense melon or kiwi-like fruity note, a fresh marine note and a rose-like floral note, and is also excellent in persistence.

In this manner, the compound represented by formula (1) has an excellent aroma with a fruity note and the like and is also excellent in persistence, and hence can be used, singly or in combination with another component, as an aroma component for various products such as perfumery and cosmetics products, health and hygiene materials, miscellaneous goods, drinks, foods, quasi-drugs and pharmaceuticals. Specifically, the compound can be used as a perfuming ingredient of soap, a shampoo, a rinse, a detergent, cosmetics, a spray product, an aromatic, a perfume or a bath additive.

[Method for Producing Compound represented by Formula (1)]

The compound represented by formula (1) of the present embodiment can be produced by, for example, a synthesis method including, as a key step, a Diels-Alder reaction for heat-reacting an olefin and dicyclopentadiene.

Specifically, the compound represented by formula (1-1) can be produced by a Diels-Alder reaction for heat-reacting an olefin and dicyclopentadiene as follows:

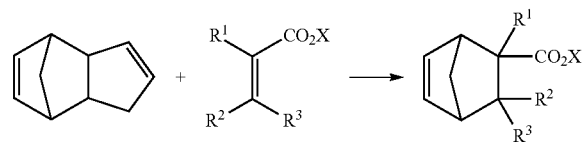

wherein $R^1$, $R^2$, $R^3$ and X have the same meaning as $R^1$, $R^2$, $R^3$ and X in formula (1). Specifically, $R^1$, $R^2$ and $R^3$ are independently hydrogen or a methyl group, and X is an alkyl group having 1 to 4 carbon atoms.

Examples of the olefin include methyl acrylate, ethyl acrylate, propyl acrylate, butyl acrylate, methyl methacrylate, ethyl methacrylate, propyl methacrylate, butyl methacrylate, methyl crotonate, ethyl crotonate, propyl crotonate, butyl crotonate, methyl 3-methylcrotonate, ethyl 3-methylcrotonate, propyl 3-methylcrotonate and butyl 3-methylcrotonate. Among these olefins, methyl acrylate, ethyl acrylate, methyl methacrylate, ethyl methacrylate, methyl crotonate, ethyl crotonate, methyl 3-methylcrotonate and ethyl 3-methylcrotonate are preferred, and methyl acrylate, ethyl acrylate, methyl methacrylate and ethyl methacrylate are more preferred.

The dicyclopentadiene preferably has a higher purity, and it is desirable to avoid containment of butadiene, isoprene and the like therein as far as possible. The purity of the dicyclopentadiene is preferably 90% or more, and more preferably 95% or more. Since dicyclopentadiene is known to be changed into cyclopentadiene through depolymerization under heating conditions, cyclopentadiene may be used instead of dicyclopentadiene.

In order to cause the Diels-Alder reaction to efficiently proceed, it is significant that cyclopentadiene is present in the reaction system, and therefore, the reaction temperature is preferably 100° C. or more, more preferably 120° C. or more, and further preferably 130° C. or more.

On the other hand, in order to inhibit generation of a high boiling point substance as a byproduct, the reaction temperature is preferably 250° C. or less.

A hydrocarbon, an alcohol, an ester or the like can be used as a reaction solvent, and an aliphatic hydrocarbon having 6 or more carbon atoms, and specifically, cyclohexane, toluene, xylene, ethylbenzene, mesitylene, propanol, butanol or the like is suitably used.

As a reaction method of the Diels-Alder reaction of the present embodiment, any of various reaction methods, such as a batch method using a tank reactor or the like, a semi-batch method in which a substrate or a substrate solution is supplied to a tank reactor under reaction conditions, and a continuous flow method in which a substrate is allowed to flow to a tubular reactor under reaction conditions, can be employed.

A product obtained through the above-described reaction may be used as a perfume composition comprising the compound represented by formula (1), may be used as a starting material for a next reaction, or may be used as a perfume composition or a starting material for a next reaction after purification by distillation, extraction, crystallization or the like.

The thus obtained product, namely, the compound represented by formula (1-1), can be used as a starting material for a next reaction, and can be used as a starting material for synthesizing the compound represented by formula (1-2) or the compound represented by formula (1-3).

Specifically, the compound represented by formula (1-2) can be produced as follows by subjecting the compound represented by formula (1-1) to a hydrogenation reaction in the presence of a catalyst.

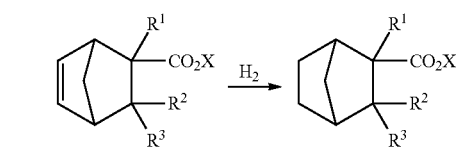

wherein $R^1$, $R^2$, $R^3$ and X have the same meaning as $R^1$, $R^2$, $R^3$ and X in formula (1). Specifically, $R^1$, $R^2$ and $R^3$ are independently hydrogen or a methyl group, and X is an alkyl group having 1 to 4 carbon atoms.

The catalyst to be used in the hydrogenation reaction is not especially limited as long as it is a catalyst usually used for hydrogenation of an unsaturated bond, and is preferably a catalyst containing at least one selected from the group 8 to 11 metals of the periodic table. A specific example includes a catalyst containing at least one of iron, cobalt, nickel, copper, ruthenium, rhodium, palladium, silver, osmium, iridium, platinum and gold.

The hydrogenation catalyst may be a solid catalyst or a homogeneous catalyst, and from the viewpoint of releasability from a reaction product, is preferably a solid catalyst. Examples of the solid catalyst include a non-supported metal catalyst and a supported metal catalyst.

The non-supported metal catalyst can be preferably a Raney catalyst such as Raney nickel, Raney cobalt or Raney copper; an oxide of platinum, palladium, rhodium or ruthenium; or a colloidal catalyst.

The supported metal catalyst is a catalyst in which at least one of, for example, iron, cobalt, nickel, copper, ruthenium, rhodium, palladium, silver, osmium, iridium, copper and gold is supported on or mixed with a support of magnesia, zirconia, ceria, diatomaceous earth, activated carbon, alumina, silica, zeolite, titania or the like.

Specific examples of the supported metal catalyst suitably include supported copper catalysts in which a copper catalyst, such as a copper-chromium catalyst (Adkins catalyst), a copper-zinc catalyst or a copper-iron catalyst, is supported on a support, supported platinum catalysts of Pt/C and Pt/alumina, supported palladium catalysts of Pd/C and Pd/alumina, supported ruthenium catalysts of Ru/C and Ru/alumina, and supported rhodium catalysts of Rh/C and Rh/alumina.

Among these catalysts, a catalyst containing copper is more preferred from the viewpoints of reaction activity and selectivity.

A use amount of the hydrogenation catalyst may be appropriately adjusted depending on the type of the catalyst, and is 0.001 to 100% by mass, preferably 0.01 to 30% by mass, and further preferably 0.1 to 20% by mass with respect to the norbornene-2-carboxylic acid ester compound used as the starting material.

A hydrogen pressure to be employed in the hydrogenation reaction may be either of normal pressure or increased pressure, and is usually normal pressure to 4.0 MPa, preferably 0.1 to 3.0 MPa, and more preferably 0.1 to 2.0 MPa.

The hydrogenation reaction may be performed in the absence of a solvent or with a solvent used.

Examples of the solvent include water, organic acids such as formic acid and acetic acid; esters such as ethyl acetate and butyl acetate; aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and a mixture of any of these.

An amount of the solvent when used in the hydrogenation reaction is usually 0.1 to 30 mass times, and preferably 0.2 to 20 mass times the amount of the norbornene-2-carboxylic acid ester compound used as the starting material.

A reaction temperature of the hydrogenation reaction can be usually −90° C. to 200° C. The reaction temperature is preferably 20° C. to 150° C., and more preferably 50° C. to 120° C.

The type of the hydrogenation reaction is not especially limited as long as a catalytic hydrogenation reaction can be performed, and any of usually employed known types may be employed. Examples of the type of the hydrogenation reaction include a type using a slurry bed reactor in which the catalytic hydrogenation reaction is performed with a catalyst allowed to flow in the form of a fluid, and a type using a fixed bed reactor in which the catalytic hydrogenation reaction is performed with a catalyst filled/fixed and with a fluid supplied.

A reaction product obtained through the hydrogenation reaction can be rectified with a distillation column after removing a low boiling point substance and the like therefrom with an evaporator or the like, and thus, the resultant can be used as the perfume composition comprising the compound represented by formula (1-2).

The compound represented by formula (1-3) can be synthesized from the compound represented by formula (1-1) as follows by performing a hydroformylation reaction of carbon monoxide and hydrogen gas in the presence of a rhodium compound and an organophosphorus compound.

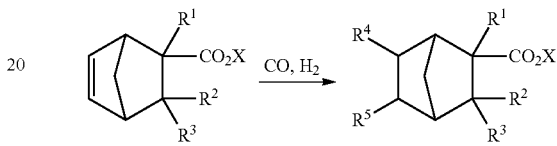

wherein $R^1$, $R^2$, $R^3$ and X have the same meaning as $R^1$, $R^2$, $R^3$ and X in formula (1). Specifically, $R^1$, $R^2$ and $R^3$ are independently hydrogen or a methyl group, and X is an alkyl group having 1 to 4 carbon atoms. Either one of $R^4$ and $R^5$ is hydrogen, and the other is a —CHO group.

The rhodium compound used in the hydroformylation reaction is not limited in the form of a precursor thereof as long as it is a compound forming a complex together with the organophosphorus compound and exhibiting hydroformylation activity in the presence of carbon monoxide and hydrogen. A catalyst precursor such as rhodium acetylacetonate dicarbonyl (hereinafter referred to as Rh(acac)(CO)$_2$), Rh$_2$O$_3$, Rh$_4$(CO)$_{12}$, Rh$_6$(CO)$_{16}$ or Rh(NO$_3$)$_3$ may be introduced into a reaction mixture together with the organophosphorus compound to form a rhodium metal hydridocarbonyl phosphorus complex having catalytic activity in a reaction vessel, or a rhodium metal hydridocarbonyl phosphorus complex may be precedently prepared to be supplied into a reactor. As a specific preferable production method of the rhodium compound used in the hydroformylation reaction, a method in which Rh(acac)(CO)$_2$ is reacted with the organophosphorus compound in the presence of a solvent, and the resultant is introduced into a reactor together with an excessive amount of the organophosphorus compound to obtain a rhodium-organophosphorus complex having catalytic activity may be employed.

An amount of the rhodium compound used in the hydroformylation reaction is preferably 0.1 to 30 micromoles, more preferably 0.2 to 20 micromoles, and further preferably 0.5 to 10 micromoles per mole of an olefin used as a substrate of the hydroformylation reaction. When the amount of the rhodium compound used is smaller than 30 micromoles per mole of the olefin, there is no need to provide recovery recycling equipment for a rhodium complex, and hence cost of the rhodium catalyst can be reduced, and thus, economic burden related to the recovery recycling equipment can be reduced. When the amount of the rhodium compound used is larger than 0.1 micromoles per mole of the olefin, a hydroformylation reaction product can be obtained in a high yield.

Examples of the organophosphorus compound used in the hydroformylation reaction for forming, together with the rhodium compound, the catalyst of the hydroformylation reaction include a phosphine represented by general formula P(—R$^6$) (—R$^7$) (—R$^8$) and a phosphite represented by general formula P(—OR$^6$) (—OR$^7$) (—OR$^6$).

Specific examples of R$^6$, R$^7$ and R$^8$ include an aryl group that may be substituted with an alkyl group having 1 to 4 carbon atoms or an alkoxy group having 1 to 4 carbon atoms, and an alicyclic alkyl group that may be substituted with an alkyl group having 1 to 4 carbon atoms or an alkoxy group having 1 to 4 carbon atoms.

Specifically, triphenylphosphine or triphenylphosphite is suitably used as the organophosphorus compound.

An amount of the organophosphorus compound used is preferably 500 times mole to 10000 times mole, more preferably 700 times mole to 5000 times mole, and further preferably 900 times mole to 2000 times mole of the rhodium metal. When the amount of the organophosphorus compound used is smaller than 500 times mole of the rhodium metal, the stability of the rhodium metal hydridocarbonyl phosphorus complex working as the catalyst active material is spoiled, and hence, the progress of the reaction tends to be slowed. When the amount of the organophosphorus compound used is larger than 10000 times mole of the rhodium metal, cost related to the organophosphorus compound tends to be increased.

The hydroformylation reaction can be performed without using a solvent, and when a solvent inert to the reaction is used, the reaction can be more suitably performed. The solvent is not especially limited as long as it dissolves an olefin, dicyclopentadiene or cyclopentadiene, and the rhodium compound and the organophosphorus compound.

Specific examples of the solvent include hydrocarbons such as aliphatic hydrocarbons, alicyclic hydrocarbons and aromatic hydrocarbons; esters such as aliphatic esters, alicyclic esters and aromatic esters; alcohols such as aliphatic alcohols and alicyclic alcohols; and aromatic halides. Among these solvents, a hydrocarbon is preferred, and an alicyclic hydrocarbon or an aromatic hydrocarbon is more preferred.

A temperature in performing the hydroformylation reaction is preferably 40° C. to 160° C., and more preferably 80° C. to 140° C. When the reaction temperature is 40° C. or more, a sufficient reaction rate can be obtained, and hence remaining of the olefin used as the starting material can be inhibited. When the reaction temperature is 160° C. or less, generation of byproducts derived from the olefin of the starting material and the reaction product is inhibited to prevent degradation of a reaction result.

For performing the hydroformylation reaction, the reaction needs to be performed under pressure of carbon monoxide (CO) and hydrogen (H$_2$) gas. The CO and the H$_2$ gas can be each independently introduced into the reaction system or can be introduced into the reaction system in the form of a mixed gas precedently prepared. A molar ratio between the CO and the H$_2$ gas (=CO/H$_2$) to be introduced into the reaction system is preferably 0.2 to 5, more preferably 0.5 to 2, and further preferably 0.8 to 1.2. If the molar ratio between the CO and the H$_2$ gas is out of this range, the reaction activity of the hydroformylation reaction and selectivity of a target aldehyde may be lowered in some cases. Since the CO and the H$_2$ gas introduced into the reaction system are reduced in accordance with the progress of the reaction, the reaction may be easily controlled in some cases by utilizing a precedently prepared mixed gas of CO and H$_2$.

A reaction pressure employed in the hydroformylation reaction is preferably 1 to 12 MPa, more preferably 1.2 to 9 MPa, and further preferably 1.5 to 5 MPa. When the reaction pressure is 1 MPa or more, a sufficient reaction rate can be obtained, and hence the olefin used as a starting material can be inhibited from remaining. When the reaction pressure is 12 MPa or less, it is economically advantageous because there is no need to use expensive equipment excellent in pressure resistance performance. In particular, when the reaction is performed by the batch method or the semi-batch method, it is necessary to discharge the CO and the H$_2$ gas and to reduce the pressure after completing the reaction, and therefore, loss of the CO and the H$_2$ gas is reduced as the pressure is lower, which is economically advantageous.

As a reaction method for performing the hydroformylation reaction, a batch reaction or a semi-batch reaction is suitably employed. The semi-batch reaction can be performed by adding the rhodium compound, the organophosphorus compound, and the solvent to the reactor, applying a pressure with a CO/H$_2$ gas and increasing a temperature to obtain the above-described reaction conditions, and then, supplying an olefin used as the starting material or a solution thereof to the reactor.

A reaction product obtained through the hydroformylation reaction can be rectified with a distillation column after removing a low boiling point substance and the like therefrom with an evaporator or the like, and thus, the resultant can be used as the perfume composition comprising the compound represented by formula (1-3).

In the perfume composition of the present embodiment, usually used another perfume component and/or a compound perfume having a desired composition may be mixed with a single one or two or more of the compounds represented by formula (1) to be blended therein.

An amount of the compound represented by formula (1) blended in the perfume composition of the present embodiment may be appropriately adjusted in accordance with the type of the compound perfume, the type and the intensity of a desired aroma and the like, and the compound is added to a compound perfume in an amount of preferably 0.01 to 90% by mass, and more preferably 0.1 to 50% by mass.

Examples of the perfume component usable in the perfume composition of the present embodiment in combination with the compound represented by formula (1) include, but are not limited to, surfactants such as polyoxyethylene lauryl ether sulfate; solvents such as dipropylene glycol, diethyl phthalate, ethylene glycol, propylene glycol, methyl myristate and triethyl citrate; hydrocarbons such as limonene, α-pinene, β-pinene, terpinene, cedrene, longifolene and valencene; alcohols such as linalool, citronellol, geraniol, nerol, terpineol, dihydromyrcenol, ethyl linalool, farnesol, nerolidol, cis-3-hexenol, cedrol, menthol, borneol, β-phenylethyl alcohol, benzyl alcohol, phenyl hexanol, 2,2, 6-trimethylcyclohexyl-3-hexanol, 1-(2-t-butylcyclohexyloxy)-2-butanol, 4-isopropylcyclohexane methanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol and 3,7-dimethyl-7-methoxyoctan-2-ol; phenols such as eugenol, thymol and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl 2-cyclohexyl propionate, benzyl propionate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyl dihydrojasmonate, methyl-2,4-dihydroxy-3,6-dimethyl benzoate, ethyl methyl phenyl glycidate, methyl anthranilate and fruitate; aldehydes such as n-octanal, n-decanal, n-dodecanal, 2-methyl undecanal, 10-undecenal, citronellal, citral, hydroxycitronellal, dimethyl tetrahydrobenzaldehyde, 4(3)-(4-hydroxy-4-methylpentyl)-3-cyclohexen-1-carboaldehyde, 2-cyclohexyl propanal, p-t-butyl-α-methyl hydrocinnamic aldehyde, p-isopropyl-α-methyl hydrocinnamic aldehyde, p-ethyl-α,α-dimethyl hydrocinnamic aldehyde, α-amyl cinnamic aldehyde, α-hexyl cinnamic aldehyde, piperonal and α-methyl-3,4-methylenedioxyhydrocinnamic aldehyde; ketones such as methyl heptenone, 4-methylene-3,5,6,6-tetramethyl-2-heptanone, amyl cyclopentanone, 3-methyl-2-(cis-2-penten-1-yl)-2-cyclopenten-1-one, methyl cyclopentenolone, rose ketone, γ-methylionone, α-ionone, carvone, menthone, camphor, nootkatone, benzyl acetone, anisyl acetone, methyl β-naphthyl ketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone and cyclohexadecenone; acetals and ketals such as acetaldehyde ethylphenylpropylacetal, citral diethylacetal, phenylacetaldehyde glycerin acetal and ethyl acetoacetate ethylene glycol ketal; ethers such as anethole, β-naphthyl methyl ether, β-naphthyl ethyl ether, limonene oxide, rose oxide, 1,8-cineole, racemic or optically active dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate and 11-oxahexadecanolide; and other perfuming substances such as natural essential oils and natural extracts of orange, lemon, bergamot, mandarin, peppermint, spearmint, lavender, chamomile, rosemary, *eucalyptus*, sage, basil, rose, geranium, jasmine, ylang ylang, anise, clove, ginger, nutmeg, cardamom, cedar, cypress, vetiver, patchouli, labdanum and the like. One of or a plurality of these perfuming substances may be blended.

The perfume composition comprising the compound represented by formula (1) can be used as an aroma component, used for purposes of imparting an aroma or improving an aroma of a target to be blended with, of various products such as perfumery and cosmetics products, health and hygiene materials, miscellaneous goods, drinks, foods, quasi-drugs and pharmaceuticals.

The perfume composition comprising the compound represented by formula (1) can be used as an aroma component of, for example, fragrance products such as a perfume and colognes; hair cosmetics such as a shampoo, a rinse, a hair tonic, a hair cream, a hair mousse, a hair gel, a pomade and a hair spray; skin cosmetics such as a skin lotion, an essence, a cream, a milky lotion, a face mask, a foundation, a face powder, a lipstick and various make-ups; a dishwashing detergent, a laundry detergent, a softener, a disinfection detergent, a deodorant detergent, an environmental fragrance, a furniture care agent, a glass cleaner, a furniture cleaner, a floor cleaner, a disinfectant, an insecticide, a bleaching agent and other detergents for various health and hygiene applications; quasi-drugs such as a dentifrice, a mouthwash, a bath additive, an antiperspirant product and a perm solution; miscellaneous goods such as toilet paper and tissue paper; pharmaceuticals; and foods.

An amount of the perfume or perfume composition of the present embodiment blended in each of the above-described products is, in terms of an amount of a formylnorbornane-2-carboxylic acid ester compound represented by formula (1), preferably 0.001 to 50% by mass, and more preferably 0.01 to 20% by mass with respect to the total amount of the product.

EXAMPLES

Now, the method of the present invention will be described in more details with reference to Examples, and it is noted that the present invention is not limited to these examples.

Measurement methods employed in the following examples are as follows:

<Conditions for Gas Chromatography Analysis>

Analysis Apparatus: capillary gas chromatograph GC-2010 Plus, manufactured by Shimadzu Corporation Analysis Column: Inert Cap1 (30 m, 0.32 mm I.D., film thickness: 0.25 μm, manufactured by GL Sciences Inc.)

Oven Temperature: 60° C. (0.5 min)—temperature increase rate 15° C./min—280° C. (4 min)

Detector: FID, temperature: 280° C.

<Yield and Selectivity of Carboxylic Acid Ester Compound>

Gas chromatography analysis was performed to obtain an area ratio (GC %) of a product, that is, a carboxylic acid ester compound, and the yields and selectivities of norbornene-2-carboxylic acid ester and a norbornane-2-carboxylic acid ester compound were calculated by an internal standard method in accordance with the following expressions:

Yield (mol %) in terms of olefin=obtained amount (mol) of norbornene-2-carboxylic acid ester/ charged amount (mol) of olefin×100

Yield (mol %) in terms of dicyclopentadiene=obtained amount (mol) of norbornene-2-carboxylic acid ester/charged amount (mol) of dicyclopentadiene×100/2

Selectivity (mol %) in terms of olefin=obtained amount (mol) of norbornene-2-carboxylic acid ester/reacted amount (mol) of olefin×100

Selectivity (mol %) in terms of dicyclopentadiene=obtained amount (mol) of norbornene-2-carboxylic acid ester/reacted amount (mol) of dicyclopentadiene×100/2

Yield (mol %) in hydrogenation reaction=obtained amount (mol) of norbornane-2-carboxylic acid ester/charged amount (mol) of norbornene-2-carboxylic acid ester×100

Selectivity (mol %) in hydrogenation reaction=obtained amount (mol) of norbornane-2-carboxylic acid ester/reacted amount (mol) of norbornene-2-carboxylic acid ester×100

Yield (mol %) in hydroformylation reaction=obtained amount (mol) of formylnorbornane-2-carboxylic acid ester/charged amount (mol) of norbornene-2-carboxylic acid ester× 100

Selectivity (mol %) in hydroformylation reaction=obtained amount (mol) of formylnorbornane-2-carboxylic acid ester/reacted amount (mol) of norbornene-2-carboxylic acid ester× 100

<Conditions for GC-MS Measurement>
Analysis Apparatus: GCMS-QP2010 Plus, manufactured by Shimadzu Corporation
Ionization Potential: 70 eV
Analysis Column: DB-1 (30 m, 0.32 mm I.D., film thickness 1.00 μm), manufactured by Agilent Technologies
Oven Temperature: 60° C. (0.5 min)—temperature increase rate 15° C./min—280° C. (4 min)

Example 1

(Synthesis Method of Norbornene-2-Carboxylic Acid Methyl Ester)

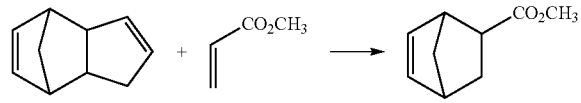

Synthesis was performed by using a stainless steel autoclave having an internal volume of 500 ml and equipped with a magnetic induction stirrer and three inlet nozzles disposed in an upper portion.

First, the autoclave was charged with 101.2 g of n-dodecane (special grade reagent, manufactured by Tokyo Chemical Industry Co., Ltd.), and after nitrogen gas replacement, the resultant was heated to a liquid temperature of 195° C.

With the reaction temperature kept at 195° C., a mixture of 96.4 g (1.12 mol) of methyl acrylate and 105.7 g (0.80 mol) of dicyclopentadiene was supplied from the upper portion of the autoclave over 1 hour, and the resultant was continuously stirred for 2 hours.

After cooling the reaction solution, 301.0 g of the resultant solution was analyzed by a gas chromatography internal standard method, resulting in finding that a norbornene-2-carboxylic acid methyl ester compound of a target was contained therein in an amount of 133.2 g. As a result in terms of methyl acrylate, the yield was 78.2% by mol and the selectivity was 79.0% by mol, and as a result in terms of dicyclopentadiene, the yield was 54.7% by mol and the selectivity was 59.3% by mol.

The thus obtained liquid was rectified by using a distillation column having 20 theoretical plates (distillation temperature: 88° C., degree of vacuum: 2.7 kPa), and a main distillate portion having 98.5 GC % by the gas chromatography analysis was obtained in an amount of 120.5 g (distillation yield: 90.5% by mol).

The resultant fraction was analyzed by the GC-MS, resulting in finding a molecular weight of 152 of the target.

The thus obtained fraction had a novel aroma including both a ripe banana and melon-like fruity note and an ozone-like marine note differently from known fruitate having a fruity aroma alone or known geranyl acetate having a rose-like aroma alone, and was characterized by excellent aroma persistence superior to the other known esters or geranyl acetate.

(Apricot-Like Fruity Perfume Composition Having Floral Note)

First, a perfume composition (a control) having a composition listed in Table 1 was produced. Next, 10 parts by mass of the norbornene-2-carboxylic acid methyl ester prepared as described above was added to 90 parts by mass of the control to prepare a perfume composition.

The thus obtained perfume composition was verified, through aroma evaluation by a perfumer, to have an apricot-like fruity scent having a gorgeous gardenia-like floral note.

TABLE 1

| Ingredient | Parts by mass |
| --- | --- |
| Benzyl Alcohol | 25 |
| Linalool | 20 |
| ε-Decanolactone | 17 |
| Tricyclodecan-2-carboxylic Acid Ethyl | 15 |
| Benzyl Acetate | 5 |
| Isobutyl Acetate | 3 |
| Diethyl Malonate | 2 |
| β-Ionone | 2 |
| Limonene | 1 |
| Total | 90 |

Example 2

(Synthesis Method of Norbornene-2-Methyl-2-Carboxylic Acid Methyl Ester)

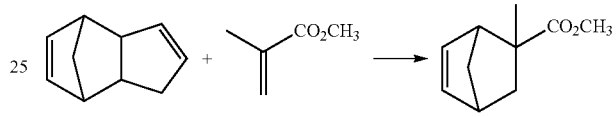

The Diels-Alder reaction and the treatment were performed in the same manner as in Example 1 except that 112.1 g (1.12 mol) of methyl methacrylate was used as the olefin.

After cooling the reaction solution, 316.9 g of the resultant solution was analyzed by the gas chromatography internal standard method, resulting in finding that a norbornene-2-methyl-2-carboxylic acid methyl ester compound of a target was contained therein in an amount of 140.0 g. As a result in terms of methyl methacrylate, the yield was 75.2% by mol and the selectivity was 75.9% by mol, and as a result in terms of dicyclopentadiene, the yield was 52.7% by mol and the selectivity was 57.4% by mol.

The thus obtained liquid was rectified by using a spinning band distillation column having 40 theoretical plates (distillation temperature: 90° C., degree of vacuum: 2.7 kPa), and a main distillate portion having 98.5 GC % by the gas chromatography analysis was obtained in an amount of 127.5 g (distillation yield: 91.1% by mol).

The resultant fraction was analyzed by the GC-MS, resulting in finding a molecular weight of 166 of the target.

The thus obtained fraction had a novel aroma including both a fresh floral green note and a fruity note differently from known fruitate having a fruity aroma alone or known geranyl acetate having a rose-like aroma alone, and was characterized by excellent aroma persistence superior to the other known esters or geranyl acetate.

(Perfume Composition Having Fruity Scent Like Fresh Pear)

First, a perfume composition (a control) having a composition listed in Table 2 was produced. Next, 10 parts by mass of the norbornene-2-methyl-2-carboxylic acid methyl ester prepared as described above was added to 90 parts by mass of the control to prepare a perfume composition.

The thus obtained perfume composition was verified, through aroma evaluation by a perfumer, to have a fruity scent like a fresh pear.

TABLE 2

| Ingredient | Parts by mass |
| --- | --- |
| Tricyclodecan-2-carboxylic Acid Ethyl | 30 |
| Cyclopentadecanone | 14 |
| Isobutyl Acetate | 12 |
| Allyl Heptanoate | 10 |
| ε-Decanolactone | 10 |
| β-Ionone | 5 |
| Benzyl Alcohol | 3 |
| Isopropyl Cyclohexanol | 3 |
| Ethyl Acetoacetate | 2 |
| Limonene | 1 |
| Total | 90 |

Example 3

(Synthesis Method of Norbornane-2-carboxylic Acid Methyl Ester)

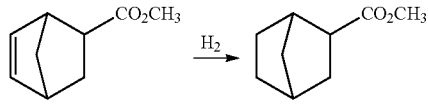

A hydrogenation reaction was performed by using a stainless steel autoclave having an internal volume of 500 ml and equipped with a magnetic induction stirrer and three inlet nozzles disposed in an upper portion.

The autoclave was charged with 6.0 g of a Cu—Cr catalyst (N-203S manufactured by JGC Corporation) and 120.0 g of isopropyl alcohol (special grade reagent, manufactured by Wako Pure Chemical Industries Ltd.), and activation was performed at 170° C. and a hydrogen pressure of 2 MPa for 1 hour. After cooling, 60.0 g of the norbornene-2-carboxylic acid methyl ester prepared as described above was charged, and a reduction reaction was performed at 120° C. and a hydrogen pressure of 2 MPa for 3 hours under stirring. The thus obtained reaction solution was filtered to remove the catalyst, and thus, 173.9 g of a reaction solution containing 57.6 g of norbornane-2-carboxylic acid methyl ester was obtained (conversion rate: 100%, yield: 96.2%). As a result in terms of the norbornene-2-carboxylic acid methyl ester, the yield was 96.26% by mol, and the selectivity was 100% by mol.

The thus obtained liquid was rectified by using a spinning band distillation column having 40 theoretical plates (distillation temperature: 89° C., degree of vacuum: 2.7 kPa), and a main distillate portion having 98.5 GC % by the gas chromatography analysis was obtained in an amount of 53.5 g (distillation yield: 91.5% by mol).

The resultant fraction was analyzed by the GC-MS, resulting in finding a molecular weight of 154 of the target.

The thus obtained fraction had a herbal green-like novel aroma having an intense fruity note differently from known fruitate having a fruity aroma alone or known geranyl acetate having a rose-like aroma alone, and was characterized by excellent aroma persistence superior to the other known esters or geranyl acetate.

(Perfume Composition Having Fruity Scent with Green Apple Freshness)

First, a perfume composition (a control) having a composition listed in Table 3 was produced. Next, 10 parts by mass of the norbornane-2-carboxylic acid methyl ester prepared as described above was added to 90 parts by mass of the control to prepare a perfume composition.

The thus obtained perfume composition was verified, through aroma evaluation by a perfumer, to have a fruity scent with green apple freshness.

TABLE 3

| Ingredient | Parts by mass |
| --- | --- |
| Tricyclodecan-2-carboxylic Acid Ethyl | 30 |
| Cyclopentadecanone | 14 |
| Isobutyl Acetate | 12 |
| Allyl Heptanoate | 10 |
| ε-Decanolactone | 10 |
| β-Ionone | 5 |
| Benzyl Alcohol | 3 |
| Isopropyl Cyclohexanol | 3 |
| Ethyl Acetoacetate | 2 |
| Limonene | 1 |
| Total | 90 |

Example 4

(Synthesis Method of Formylnorbornane-2-Carboxylic Acid Methyl Ester)

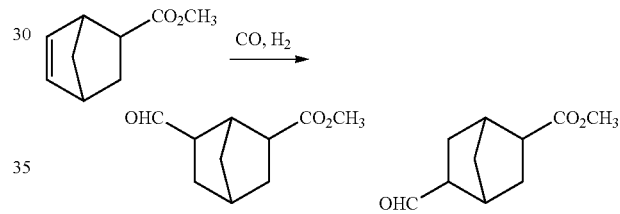

A hydroformylation reaction was performed by using a stainless steel autoclave having an internal volume of 500 ml and equipped with a magnetic induction stirrer and three inlet nozzles disposed in an upper portion.

To the autoclave, 60.0 g of the norbornene-2-carboxylic acid methyl ester prepared as described above, 116.9 g of toluene, 0.37 g of triphenyl phosphite and 3.10 g of a separately prepared toluene solution of Rh(acac) (CO)$_2$ (concentration: 0.01 wt %) were added. After performing replacement with nitrogen and CO/H$_2$ mixed gas respectively three times, the system was compressed with CO/H$_2$ mixed gas, and a reaction was performed at 100° C. and 2 MPa for 5 hours. After completing the reaction, the resultant reaction solution was subjected to the gas chromatography analysis to obtain 186.9 g of the reaction solution containing 69.0 g of formylnorbornane-2-carboxylic acid methyl ester (a mixture of 5-formylnorbornane-2-carboxylic acid methyl ester and 6-formylnorbornane-2-carboxylic acid methyl ester). As a result in terms of norbornene-2-carboxylic acid methyl ester, the yield was 96.2% by mol, and the selectivity was 100% by mol.

The thus obtained liquid was rectified by using a spinning band distillation column having 40 theoretical plates (distillation temperature: 112° C., degree of vacuum: 0.19 kPa), and a main distillate portion having 98.4 GC % by the gas chromatography analysis was obtained in an amount of 63.5 g (distillation yield: 90.7% by mol).

The resultant fraction was analyzed by the GC-MS, resulting in finding a molecular weight of 182 of the target.

The thus obtained fraction had a novel aroma having all of an intense melon or kiwi-like fruity note, a fresh marine note and a rose-like floral note differently from known fruitate having a fruity aroma alone or known geranyl acetate having a rose-like aroma alone, and was characterized by excellent aroma persistence superior to the other known esters or geranyl acetate.

(Perfume Composition Having Fruity Scent with Sweet and Gorgeous Gardenia-Like Floral Note)

First, a perfume composition (a control) having a composition listed in Table 4 was produced. Next, 10 parts by mass of the formylnorbornane-2-carboxylic acid methyl ester prepared as described above was added to 90 parts by mass of the control to prepare a perfume composition.

The thus obtained perfume composition was verified, through aroma evaluation by a perfumer, to have a fruity scent with a sweet and gorgeous gardenia-like floral note.

TABLE 4

| Ingredient | Parts by mass |
| --- | --- |
| Benzyl Alcohol | 25 |
| Linalool | 20 |
| ε-Decanolactone | 17 |
| Tricyclodecan-2-carboxylic Acid Ethyl | 15 |
| Benzyl Acetate | 5 |
| Isobutyl Acetate | 3 |
| Diethyl Malonate | 2 |
| β-Ionone | 2 |
| Limonene | 1 |
| Total | 90 |

This application is based upon the prior Japanese patent application filed on Sep. 15, 2016 (Japanese Patent Application No. 2016-180434), Japanese patent application filed on Sep. 15, 2016 (Japanese Patent Application No. 2016-180435) and Japanese patent application filed on Sep. 15, 2016 (Japanese Patent Application No. 2016-180436), the entire contents of which are incorporated herein by reference.

INDUSTRIAL APPLICABILITY

A carboxylic acid ester compound having a norbornane skeleton of the present invention has a fruity aroma and excellent aroma persistence, and therefore is useful as a perfuming ingredient for a variety of products including toiletries, soap and laundry detergents.

The invention claimed is:

1. A perfume composition, comprising:
an aroma component comprising a compound of formula (1-3),

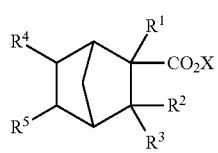

(1-3)

wherein each of $R^1$, $R^2$ and $R^3$ is hydrogen, X is $CH_3$, and one of $R^4$ and $R^5$ is hydrogen, and the other one of $R^4$ and $R^5$ is a —CHO group.

2. The perfume composition according to claim 1, wherein the aroma component further includes at least one compound selected from the group consisting of formulas (1-1) and (1-2),

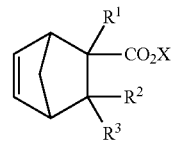

(1-1)

wherein where $R^1$, $R^2$ and $R^3$ are independently hydrogen or a methyl group, and X is an alkyl group having 1 to 4 carbon atoms,

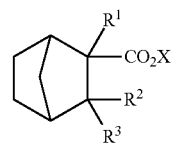

(1-2)

where $R^1$, $R^2$ and $R^3$ are independently hydrogen or a methyl group, and X is an alkyl group having 1 to 4 carbon atoms.

3. A perfumery and cosmetics product, comprising:
the perfume composition of claim 2.
4. A health and hygiene material, comprising:
the perfume composition of claim 2.
5. A perfumery and cosmetics product, comprising:
the perfume composition of claim 1.
6. A health and hygiene material, comprising:
the perfume composition of claim 1.
7. A drink, comprising:
the perfume composition of claim 1.
8. A food, comprising:
the perfume composition of claim 1.
9. A quasi-drug, comprising:
the perfume composition of claim 1.
10. A pharmaceutical, comprising:
the perfume composition of claim 1.
11. A miscellaneous good, comprising:
the perfume composition of claim 1.
12. The perfume composition according to claim 1, wherein the aroma component further includes a compound of formula (1-1),

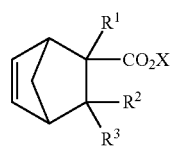

(1-1)

where $R^1$, $R^2$ and $R^3$ are independently hydrogen or a methyl group, and X is an alkyl group having 1 to 4 carbon atoms.
13. A perfumery and cosmetics product, comprising:
the perfume composition of claim 12.
14. A health and hygiene material, comprising:
the perfume composition of claim 12.
15. The perfume composition according to claim 1, wherein the aroma component further includes a compound of formula (1-2),

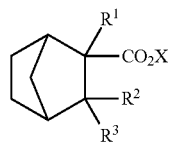

(1-2)

where $R^1$, $R^2$ and $R^3$ are independently hydrogen or a methyl group, and X is an alkyl group having 1 to 4 carbon atoms.

16. A perfumery and cosmetics product, comprising:
the perfume composition of claim 15.

17. A health and hygiene material, comprising:
the perfume composition of claim 15.

18. The perfume composition according to claim 1, wherein the aroma component further includes a compound of formula (1-1),

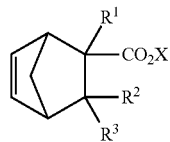

(1-1)

where $R^1$, $R^2$ and $R^3$ are independently hydrogen or a methyl group, and X is an alkyl group having 1 to 4 carbon atoms, and a compound of formula (1-2),

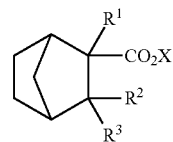

(1-2)

where $R^1$, $R^2$ and $R^3$ are independently hydrogen or a methyl group, and X is an alkyl group having 1 to 4 carbon atoms.

19. A perfumery and cosmetics product, comprising:
the perfume composition of claim 18.

20. A health and hygiene material, comprising:
the perfume composition of claim 18.

* * * * *